United States Patent
Neumann et al.

(10) Patent No.: US 7,112,703 B2
(45) Date of Patent: Sep. 26, 2006

(54) PRODUCTION OF BISPHENOL-A WITH REDUCED SULFUR CONTENT

(75) Inventors: Rainer Neumann, Bad Tölz (DE); Ulrich Blaschke, Krefeld (DE); Stefan Westernacher, Kempen (DE)

(73) Assignee: Bayer MaterialScience AG, Leverkusen (DE)

( * ) Notice: Subject to any disclaimer, the term of this patent is extended or adjusted under 35 U.S.C. 154(b) by 8 days.

(21) Appl. No.: 11/043,800

(22) Filed: Jan. 26, 2005

(65) Prior Publication Data

US 2005/0215833 A1     Sep. 29, 2005

(30) Foreign Application Priority Data

Feb. 5, 2004   (DE) .................. 10 2004 005 723

(51) Int. Cl.
*C07C 39/16*     (2006.01)
(52) U.S. Cl. .................................... 568/728
(58) Field of Classification Search ............ 568/728, 568/727; 528/196
See application file for complete search history.

(56) References Cited

U.S. PATENT DOCUMENTS

| | | | | |
|---|---|---|---|---|
| 4,191,843 A * | 3/1980 | Kwantes et al. | ............. | 568/728 |
| 4,847,432 A | 7/1989 | Faler | ................... | 568/727 |
| 4,935,173 A * | 6/1990 | Huey et al. | ............... | 264/14 |
| 5,008,470 A * | 4/1991 | Powell et al. | .............. | 568/727 |
| 5,059,721 A * | 10/1991 | Powell et al. | .............. | 568/724 |
| 6,294,702 B1 * | 9/2001 | Fennhof et al. | ............ | 568/727 |
| 6,414,198 B1 * | 7/2002 | Lanze et al. | ................ | 568/724 |
| 6,653,513 B1 | 11/2003 | Iwahara | ................ | 568/728 |
| 6,828,465 B1 * | 12/2004 | Neumann et al. | .......... | 568/724 |
| 2003/0038094 A1 * | 2/2003 | Neumann et al. | .......... | 210/768 |

FOREIGN PATENT DOCUMENTS

EP          552518 B1 *  9/1995
WO   WO 200172677 A1 * 10/2001

OTHER PUBLICATIONS

"Kirk-Othmer Encyclopedia of Chemical Technology," 4th Ed., vol. 19, pp. 584-599 (1996).*
Database WPI Section Ch, Week 197917 Derwent Publications Ltd., London, GB; AN 1979-32561B XP002330403 & JP 54 036363 A (Adeka Argus Ind KK) (Mar. 17, 1979).

* cited by examiner

*Primary Examiner*—Samuel Barts
*Assistant Examiner*—Kellette Gale
(74) *Attorney, Agent, or Firm*—Bayer Material Science LLC; Aron Preis

(57) ABSTRACT

A process for the production of bisphenol-A having low concentration of sulphur is disclosed. The process comprise a) reacting phenol with acetone in the presence of a sulfonic acid ion exchanger to form a product mixture containing water, bisphenol-A/phenol adduct, phenol and sulfurous particles, and b) filtering the product mixture to separate the sulfurous particles to obtain a purified product mixture that contains water, phenol and bisphenol-A/phenol adduct. In one embodiment of the process further comprise distilling the purified product mixture to remove the water to obtain a first material system that contains said adduct and phenol, crystallizing the adduct, and removing the phenol by filtration using a filtering apparatus to obtain crystalline adduct. In a yet additional embodiment the process comprise crystallizing the purified product mixture to obtain a second material system that contains crystalline adduct, water and phenol and removing the phenol and water by filtration using a filtering apparatus to obtain crystalline adduct.

20 Claims, No Drawings

PRODUCTION OF BISPHENOL-A WITH REDUCED SULFUR CONTENT

FIELD OF THE INVENTION

The invention relates to bisphenol-A and to a process for its production.

TECHNICAL BACKGROUND OF THE INVENTION

Bisphenols as condensation products of phenols and carbonyl compounds are starting substances or intermediates for the production of a large number of commercial products. Of particular industrial significance is the condensation product of the reaction between phenol and acetone, 2,2-bis (4-hydroxyphenyl)propane (bisphenol-A, BPA). BPA is used as a starting substance for the production of various types of polymer materials, such as e.g. polyarylates, polyether imides, polysulfones and modified phenol-formaldehyde resins. Preferred areas of application lie in the production of epoxy resins and polycarbonates.

Industrially relevant production methods for BPA are known and are based on the acid-catalysed reaction of phenol with acetone, wherein a phenol-acetone ratio of more than 5:1 is preferably established in the reaction. This reaction conventionally takes place continuously, and generally at temperatures of 45 to 110° C., preferably at 50 to 80° C. Both homogeneous and heterogeneous Bronsted or Lewis acids, such as, for example, strong mineral acids, e.g. hydrochloric or sulfuric acid, may be used as acid catalysts. Gel-like or macroporous sulfonated crosslinked polystyrene resins (acid ion exchangers) are preferably used, which may be both monodisperse and heterodisperse. Divinylbenzene is normally used as the crosslinking agent, but other crosslinking agents, such as divinylbiphenyl, may also be employed. In addition to the catalyst, a co-catalyst may be used. These are usually thiols, which carry at least one SH function and have a positive effect on both the selectivity and the reactivity of the reaction. The co-catalyst may be both homogeneously dissolved in the reaction solution and, in the case of the acid ion exchangers, fixed on the catalyst itself. Homogeneous co-catalysts are e.g. mercaptopropionic acid, hydrogen sulfide, alkyl sulfides, such as e.g. ethyl sulfide, and similar compounds. Fixed co-catalysts are aminoalkyl thiols and pyridylalkyl thiols which are ionically bonded to the catalyst, it being possible for the SH function to be protected and only released during or after fixing to the catalyst, such as e.g. in the case of dimethylthiazolidine. The co-catalyst may also be covalently bonded to the catalyst as alkyl or aryl thiol.

When phenol is reacted with acetone in the presence of acid catalysts, a product mixture is formed which, in addition to unreacted phenol and possibly acetone, primarily contains BPA and water. In addition, small quantities of typical by-products of the condensation reaction occur, such as e.g. 2-(4-hydroxyphenyl)-2-(2-hydroxyphenyl)propane (o,p-BPA), substituted indanes, hydroxyphenylindanols, hydroxyphenylchromanes, spirobisindanes, substituted indenols, substituted xanthenes and more highly condensed compounds with three or more phenyl rings in the molecular backbone. In addition, other secondary components, such as anisole, mesityl oxide, mesitylene and diacetone alcohol, may form by self-condensation of the acetone and reaction with impurities in the raw materials. For economic and technical reasons, the reaction is usually performed in such a way that a hundred per cent conversion of the acetone is not achieved and 0.1–0.6 wt. % acetone is still contained in the reactor discharge.

The above-mentioned by-products, such as water, and unreacted feedstocks, such as phenol and acetone, impair the suitability of BPA for the production of polymers and have to be separated off by suitable processes. High demands are made of the purity of the raw material BPA, particularly for the production of polycarbonate.

One processing and purification method for BPA takes place by separating BPA out of the reaction mixture in the form of an approximately equimolar crystalline adduct with phenol by cooling the reaction mixture, allowing the BPA-phenol adduct to crystallise out in a suspension crystallisation. The BPA-phenol adduct crystals are then separated from the liquid phase by suitable apparatus for solid-liquid separation, such as rotary filters or centrifuges, and passed on for further purification.

Adduct crystals obtained in this way typically exhibit a purity of >99 wt. % BPA, based on the sum of BPA and the secondary components, with a phenol proportion of approx. 40 wt. %. By washing with suitable solutions, which typically contain one or more components from the group consisting of acetone, water, phenol, BPA and secondary components, the adduct crystals may be freed of impurities adhering to the surface.

The liquid stream forming during the solid-liquid separation (mother liquor) contains phenol, BPA, water formed during the reaction and unreacted acetone, and is enriched in the secondary components typically forming during BPA production. This mother liquor stream is generally fed back into the reaction unit. To maintain the catalytic activity of the acid ion exchangers, water that has formed is removed by distillation, and any acetone still present is also removed from the mother liquor at the same time. The dehydrated reaction stream thus obtained is supplemented with phenol, acetone and optionally co-catalyst and is fed back into the reaction unit. However, the phenol may also be added, wholly or partly, before the dehydration. Alternatively, water and acetone may also be removed by distillation before carrying out the suspension crystallization of the BPA-phenol adduct. In the distillation steps mentioned, a partial quantity of the phenol present in the reaction solution and, depending on its nature, optionally part or all of the co-catalyst may also be removed by distillation at the same time. In a circulating operation of this type, the problem occurs that by-products from BPA production become concentrated in the circulating stream and lead to the deactivation of the catalyst system and to poorer product qualities. To avoid excessive concentration of secondary components in the circulating stream, a partial quantity of the circulating stream—optionally after partial or complete recovery of phenol by distillation—is discharged from the process chain as so-called BPA resin.

Furthermore, part or all of the circulating stream may be passed through a rearrangement unit filled with acid ion exchanger after the solid-liquid separation and before or after the separation of water and residual acetone. This unit is generally operated at higher temperatures than the reaction unit. In this rearrangement unit, some of the secondary components from BPA production present in the circulating stream are isomerised to BPA under the prevailing conditions, so that the total yield of BPA may be increased.

For the further recovery of secondary components, the resin may also be subjected to thermal, acid- or base-catalysed cleavage. The phenol released in this case, and optionally also isopropenylphenol, may be separated off by distillation and returned to the reaction.

The BPA-phenol adduct crystals obtained following the suspension crystallisation of the reaction solution and solid-liquid separation described above are fed into further purification steps, wherein the separation of phenol and optionally the reduction of the concentration of secondary components are achieved.

Thus, the BPA-phenol adduct crystals may be recrystallized for further purification from phenol, organic solvents, water or mixtures of the above solvents, which may optionally also contain BPA and its isomers, by a suspension crystallization. By selecting suitable solvents, the phenol present in the adduct crystals may also be completely or partly removed at the same time. Any phenol remaining in the BPA after the recrystallization is then separated off completely by suitable distillation, desorption or extraction methods.

Alternatively, the phenol may also be removed from the BPA-phenol adduct crystals by melting-out processes.

After separating off the phenol, a bisphenol-A melt is obtained, which may be used for the production of polycarbonate by the transesterification process (melt polycarbonate) without previous solidification. However, the bisphenol-A melt may also be solidified by known processes, e.g. by the prilling process or by flaking, for sale or further use. The melt may also be dissolved in sodium hydroxide solution and used for the production of polycarbonate by the interfacial polycondensation process.

The bisphenol-A that has been freed of phenol may optionally be subjected to another purification step, such as e.g. melt crystallization, distillation and/or recrystallization from phenol, water or an organic solvent, such as e.g. toluene, or mixtures of these substances, before further processing.

Where a sulfonic-acid ion exchanger and/or a sulfurous co-catalyst is used, it is observed that sulfurous compounds are carried through to the bisphenol-A end product and may thus lead to quality problems relating to color. These compounds may be degradation products of the sulfonic acid ion exchanger, such as sulfuric acid, arylsulfonic acids, oligomeric polystyrene sulfonic acids, fine-particle catalyst and similar. Co-catalysts that are homogeneously present in the reaction mixture, such as e.g. mercaptopropionic acid, silyl-methanethiols, hydrogen sulfide, alkyl sulfides, such as e.g. ethyl sulfide, and similar compounds may be present in their original form or in the form of their degradation products or derivative products. Thus, the SH group may be alkylated, but compounds such as dimethyl sulfide or disulfidic compounds, elemental sulfur, thio ethers, $H_2S$ as a cleavage product from the co-catalyst and other compounds may also be involved.

The same applies to co-catalysts fixed to the catalyst, such as e.g. thiazolidines, amino(alkyl) thiols, (the above compounds may also be used in the form of their hydrochlorides and/or with an SH function masked e.g. by acyl, benzyl or tert.-butyl groups, but in which this may readily be released again), pyridyl(alkyl) thiols, alkylcarbamoylalkyl thioesters, covalently bonded aryl or alkyl thiols. These may be split off and/or destroyed and/or simply washed out in the case of the ionically bonded co-catalysts.

In the further course of bisphenol-A production and handling, particularly when bisphenol-A and product streams containing bisphenol-A are subjected to thermal stress, this may lead to undesirable reactions, cleavages and the like, which may, for example, lead to a reduction in product purity, measured as the p,p-BPA content in the end product, as well as to the colour formation already mentioned.

The object of the present invention was therefore to provide a process for the production of bisphenol-A in which the sulfur content in the bisphenol-A end product is reduced. It was also the object of the present invention to provide bisphenol-A having a residual sulfur content of <2 ppm.

SUMMARY OF THE INVENTION

A process for the production of bisphenol-A having low concentration of sulphur is disclosed. The process comprise a) reacting phenol with acetone in the presence of a sulfonic acid ion exchanger to form a product mixture containing water, bisphenol-A/phenol adduct, phenol and sulfurous particles, and b) filtering the product mixture to separate the sulfurous particles to obtain a purified product mixture that contains water, phenol and bisphenol-A/phenol adduct. In one embodiment of the process further comprise distilling the purified product mixture to remove the water to obtain a first material system that contains said adduct and phenol, crystallizing the adduct, and removing the phenol by filtration using a filtering apparatus to obtain crystalline adduct. In a yet additional embodiment the process comprise crystallizing the purified product mixture to obtain a second material system that contains crystalline adduct, water and phenol and removing the phenol and water by filtration using a filtering apparatus to obtain crystalline adduct.

DETAILED DESCRIPTION OF THE INVENTION

The invention relates to a process for the production of bisphenol-A, comprising
a) reacting phenol with acetone in the presence of a sulfonic acid ion exchanger to form a product mixture containing water, bisphenol-A/phenol adduct, phenol and sulfurous particles, and
b) filtering the product mixture to separate the sulfurous particles to obtain a purified product mixture that contains water, phenol and bisphenol-A/phenol adduct.

In one embodiment the process further comprise distilling the purified product mixture to remove the water to obtain a first material system that contains said adduct and phenol, crystallizing the adduct, and removing the phenol by filtration using a filtering apparatus to obtain crystalline adduct.

In a yet additional embodiment the inventive process comprise crystallizing the purified product mixture to obtain a second material system that contains crystalline adduct, water and phenol and removing the phenol and water by filtration using a filtering apparatus to obtain crystalline adduct.

Using the process according to the invention, bisphenol-A with sulfur contents of <2 ppm (measured by chemiluminescence) is produced.

The term sulfur content here means the content of total sulfur, calculated as the weight of the sulfur atoms, regardless of whether the sulfur is elemental or is present in the form of inorganic or organic sulfur compounds.

In the process according to the invention, filter media are used in step b) after the reaction mixture has left the reactor with the sulfonic acid ion exchanger. In these filter media, sulfurous particles may be filtered out and/or acid components neutralized, absorbed and/or adsorbed.

Gravel and/or sand beds, filter cloths and/or filter candles and/or bag filters and/or plate filters made of materials that are dimensionally stable up to 100° C., beds filled with aluminium oxide-containing materials, basic ion exchangers, particularly preferably based on polystyrene, may be used as filter media, preferably with a filtration grade of <200 µm.

The reaction mixture is then fed into a suspension crystallization to separate off the BPA-phenol adduct crystals. The cooling maybe achieved here by heat exchangers, but also by evaporation of solvents present in the reaction mixture or optionally added, such as phenol, water, alkanes or mixtures thereof. This crystallization may take place in one or more crystallizers connected in series. The total residence time of the reaction mixture in this crystallization step should preferably be more than 3 hours. An appropriately slow crystallization enables the inclusion of reaction mixture or the incorporation of impurities in the BPA-phenol adduct crystals to be avoided to the greatest extent.

The reaction mixture may optionally be completely or partly freed from water content by (vacuum) distillation prior to the suspension crystallization. A further separation of sulfurous components from the reaction mixture may also take place in this step.

By using filter media that are suitable for the separation of solids, the bisphenol-A-phenol mixed crystals (bisphenol-A-phenol adduct) are separated from the mother liquor. It is also preferably possible to wash the separated solid in or on this apparatus. This maybe achieved e.g. in appropriate centrifuges, such as trailing-blade centrifuges, screen-conveyor centrifuges or pusher centrifuges, but also on rotary filters, band filters and (vacuum) disk filters. Rotary pressure filters are preferably used, particularly preferably rotary vacuum filters.

The filter cake consisting of the bisphenol-A-phenol mixed crystals is additionally washed preferably with fresh phenol. This reduces the residual proportion of sulfurous mother liquor in the mixed crystals. The quantity of fresh phenol for washing the filtered bisphenol-A-phenol mixed crystals is preferably selected such that the rinse quantity corresponds to 50–150 wt. % of the filter cake or of the quantity filtered off. The bisphenol-A with low sulfur contents produced by the process according to the invention displays particularly positive properties if the quantity of fresh phenol, i.e. phenol introduced into the process from the outside, selected to wash the bisphenol-A-phenol mixed crystals corresponds to more than 70 wt. % of the total fresh phenol fed into the process from the outside. The washing is preferably performed at a phenol temperature of 40–70° C.

The washed mixed crystals are then preferably melted and the melt obtained is freed of phenol. The melt is preferably treated by concentration by evaporation and residual phenol desorption at temperatures of between 160 and 210° C., during which phenol and sulfur compounds are separated off. As a result of this two-step operation, in which the melt is subjected in the first step to both a vacuum and elevated temperature and in the second step to elevated temperature and a desorption gas, preferably nitrogen, not only the phenol but especially also sulfur compounds may be separated off effectively. By cooling, separating off the phenol and washing the gas fed in counter-current to the bisphenol-A-phenol melt with a suitable washing liquid, such as e.g. water, any sulfur compounds still present may be separated off.

In this way, bisphenol A melts with sulfur contents of <2 ppm may be produced by the process according to the invention.

The sulfur content of the bisphenol-A may optionally be reduced even further by a prilling process. Here, the bisphenol-A is solidified in the form of drops by free fall in a cooled nitrogen counter-current. It has been observed during this process that the nitrogen removes any sulfur still present in the product. This effect is not achieved using other solidification processes, such as e.g. flake rolling.

The invention also relates to bisphenol-A with a sulfur content of <2 ppm, which is preferably present in the form of prills.

Bisphenol-A with a low sulfur content of <2 ppm, which has been produced e.g. by the process according to the invention, may be reacted with phosgene by the interfacial polycondensation process or with diaryl carbonates, preferably diphenyl carbonate, by the melt process to form polycarbonate. During this process, no unpleasant odours arise due to sulfurous components, which occur under the high thermal stress during the production and processing of polycarbonate.

The invention is further illustrated but is not intended to be limited by the following examples in which all parts and percentages are by weight unless otherwise specified.

EXAMPLES

Example 1

Phenol and acetone are reacted on Lewatit SC 104® from Bayer Chemicals AG as sulfonic acid ion exchanger and with 300 ppm mercaptopropionic acid as co-catalyst. The reaction solution is filtered at 75° C. using a bag filter made of polypropylene with a 50 µm pore size. In a subsequent suspension crystallization with a residence time of more than three hours, the BPA-phenol adduct crystals formed in the acid-catalysed reaction of phenol and acetone with subsequent suspension crystallization are separated from the liquid phase by a rotary filter and then purified and fed into a separating unit for the separation of BPA from phenol.

Filtration is performed using a phenol- and temperature-resistant filter cloth (double calendered) with an air permeability of 700 l/dm$^2$/min. The vacuums are 100 mbar in the intake zone, 80 mbar in the washing zone and 100 mbar in the dry suction zone. The rotary filter housing is rendered inert under a slight excess pressure of 10 mbar using nitrogen (<1 ppm oxygen).

The rotary drum speed, filter cake thickness, quantity of circulating nitrogen (oxygen content <1 ppm) and the suction apertures in the control disk are adjusted such that the residual moisture in the filter cake is <15%, based on the quantity of mixed crystals. In addition, the roundness of the drum and the doctor blade alignment allow a maximum gap between doctor blade and drum of about 5 mm over the entire filter area.

Pure phenol at a temperature of 55° C. is used to rinse the filter cake in the washing zone, the rinsing quantity for cleaning of the filter cake being 100%, based on the filter cakes. The quantity of fresh phenol used to rinse the filter cake corresponds to 74% of the total quantity of fresh phenol fed into the process. For the optimum washing of the filter cake, 20 washing nozzles are used, said nozzles being arranged in such a way that their spray cones overlap on the filter cake. Nitrogen (oxygen content <1 ppm) is passed through the washed filter cake and is circulated, with about 7% of the circulating quantity being continuously discharged and replaced by pure nitrogen and the circulating nitrogen being washed with deionised water.

Immediately after removing the cake, the mixed crystals are melted on a heating coil under inert conditions (oxygen content <1 ppm) and the melt immediately flows down into a collecting vessel to minimize the contact time of the crystals on the hot stainless steel surface (1.4571). The surface temperature of the heating coil is about 160° C.

In a first step to remove phenol, the phenol is removed by distillation at temperatures of 120–140° C. and under a vacuum of 100–140 mbar until a phenol proportion of 15 wt. % is reached.

The mixed crystal melt with a phenol proportion of 15 wt. % is then pumped into a desorber. The temperature of the melt in the desorber is adjusted to 190° C. by melt input and heating, the temperature of the heating surfaces being 200° C.

Nitrogen ($N_2$) is used for the desorption, the quantity of nitrogen being 200 $m^3/m^3$ BPA/phenol mixture and the $N_2$ temperature being adjusted to 195° C. by preheating before entering the desorber. The nitrogen is circulated after desorption by cooling and separating off the phenol and sulfurous compounds, washed and purified of BPA or BPA-phenol sublimate by filtration. In relation to the circulating stream, a quantity of 3% $N_2$ is discharged.

The nitrogen is passed through a desorber filled with packing media in counter-current to the melt, which flows down from the top. An excess pressure of about 20 mbar is established at the head of the desorber, and the level in the desorber is set at 15 cm above the feed inlet and the packing.

To achieve a high BPA quality, it must be ensured that the oxygen content in the circulating nitrogen is less than 1 ppm and the circulating nitrogen is freed of metallic and ceramic solids abrasion in the sintered filter candles, and that the melt flow into and out of the desorber is filtered.

The bisphenol-A melt thus obtained has a residual sulfur content of <2 ppm.

Although the invention has been described in detail in the foregoing for the purpose of illustration, it is to be understood that such detail is solely for that purpose and that variations may be made therein by those skilled in the art without departing from the spirit and scope of the invention except as it may be limited by the claims.

What is claimed is:

1. A process for the production of bisphenol-A containing less than 2 ppm sulphur, comprising
    a) reacting phenol with acetone in the presence of a sulfonic acid ion exchanger in combination with mercaptopropionic acid as co-catalyst to obtain a product mixture containing water, bisphenol-A/phenol adduct, phenol, co-catalyst and sulfurous particles, and
    b) filtering the product mixture to separate the sulfurous particles to obtain a purified product mixture that contains water, phenol, co-catalyst and bisphenol-A/phenol adduct wherein the filtering is carried out by using a gravel and/or sand bed and at least one member that is dimensionally stable at temperatures up to 100° C. selected from the group consisting of filter cloth, filter candle, bag filter and late filter.

2. The process of claim 1 further comprising
    (2i) distilling the purified product mixture to remove the water to obtain a first material system that contains said adduct, co-catalyst and phenol,
    (2ii) crystallizing the adduct, and
    (2iii) removing the phenol and co-catalyst by filtration using a filtering apparatus to obtain a crystalline adducts.

3. The process of claim 1 further comprising
    (3i) crystallizing the purified product mixture to obtain a second material system that contains crystalline adduct, water, co-catalyst and phenol and
    (3ii) removing the phenol, co-catalyst and water by filtration using a filtering apparatus to obtain crystalline adduct.

4. The process of claim 2 wherein the crystallizing of the purified product mixture is characterized by a residence time longer than 3 hours.

5. The process of claim 3 wherein the crystallizing of the purified product mixture is characterized by a residence time longer than 3 hours.

6. The process of claim 2 wherein the filtering apparatus is a rotary vacuum filter.

7. The process of claim 3 wherein the filtering apparatus is a rotary vacuum filter.

8. The process of claim 2 further comprising washing the crystalline adduct.

9. The process of claim 3 further comprising washing the crystalline adduct.

10. The process of claim 8 wherein the washing takes place in or on the filtering apparatus.

11. The process of claim 9 wherein the washing takes place in or on the filtering apparatus.

12. The process according to claim 8, wherein the washing is with fresh phenol, and wherein the quantity of said fresh phenol is 50 to 150%, based on the weight of the adduct crystals.

13. The process according to claim 9, wherein the washing is with fresh phenol, and wherein the quantity of said fresh phenol is 50 to 150%, based on the weight of the adduct crystals.

14. The process of claim 12 wherein the phenol reacted in a) contains at least 70 percent relative to its weight of phenol used in the washing.

15. The process of claim 13 wherein the phenol reacted in a) contains at least 70 percent relative to its weight of phenol used in the washing.

16. The process of claim 2 further comprising melting the crystalline adduct at 160 to 210° C. and separating out at least 95 wt. % of the phenol contained in therein, to obtain bisphenol-A.

17. The process of claim 3 further comprising melting the crystalline adduct at 160 to 210° C. and separating out at least 95 wt. % of the phenol contained in therein, to obtain bisphenol-A.

18. The process of claim 16 wherein the separating takes place by distillation followed by desorption.

19. The process of claim 17 wherein the separating takes place by distillation followed by desorption.

20. The process of claim 1 wherein the bisphenol-A is in the form of prills.

* * * * *